United States Patent [19]
Hatch et al.

[11] Patent Number: 5,219,342
[45] Date of Patent: Jun. 15, 1993

[54] DISPOSABLE DIAPERS

[76] Inventors: Janell M. Hatch; Betty B. Hatch, both of 4253 Laguna Ave., Oakland, Calif. 94602

[21] Appl. No.: 538,885

[22] Filed: Jun. 14, 1990

[51] Int. Cl.$^5$ ............................................. A61F 13/15
[52] U.S. Cl. .................................. 604/370; 604/374; 604/385.1; 604/386; 604/399
[58] Field of Search ............... 604/364, 358, 367, 370, 604/372, 373, 374, 375, 385.1, 386, 389, 39, 393, 399, 376, 377, 387, 394–398, 400–402; 209/3, 2

[56] References Cited

U.S. PATENT DOCUMENTS

| | | | |
|---|---|---|---|
| 2,002,368 | 5/1935 | Fancher | 604/364 |
| 3,306,293 | 2/1967 | Marder et al. | 604/364 |
| 3,559,650 | 2/1971 | Larson | 604/364 |
| 3,636,952 | 1/1972 | George | 604/364 |
| 3,667,466 | 6/1972 | Ralph | 604/364 |
| 3,683,919 | 8/1972 | Ells | 604/364 |
| 3,814,240 | 6/1974 | Laundrie | 209/2 |
| 3,838,695 | 10/1974 | Comerford et al. | 604/364 |
| 3,874,385 | 4/1975 | Gellert | 604/364 |
| 3,890,220 | 6/1975 | Anderson | 209/3 |
| 3,952,745 | 4/1976 | Duncan | 604/364 |
| 4,303,501 | 12/1981 | Steffens | 209/2 |
| 4,305,507 | 12/1981 | Wittkopf | 209/3 |
| 4,944,734 | 7/1990 | Wallach | 604/364 |
| 4,963,140 | 10/1990 | Robertson et al. | 604/391 |
| 4,964,857 | 10/1990 | Osborn | 604/358 |
| 4,990,244 | 2/1991 | Anderson | 209/2 |

FOREIGN PATENT DOCUMENTS 0490671  10/1976  Australia ............................. 604/364

OTHER PUBLICATIONS

"Diapers and the Environment", brochure of Proctor & Gamble, publication date unknown.

Primary Examiner—Randall L. Green
Assistant Examiner—K. M. Reichle
Attorney, Agent, or Firm—Schapp and Hatch

[57] ABSTRACT

A diaper or incontinence shield having a liquid absorbent layer formed entirely of cellulose based material which is recyclable with paper products and, in another embodiment, a plastic liquid impermeable layer releasably held to the liquid absorbent layer for easy stripping off the soiled absorbent layer after use for recycling with other plastics. A woven rayon casing encloses the absorbent cellulose material and an odor and liquid proof container of recyclable cellulose base material is used to enclose the soiled absorbent layer for recycling therewith.

5 Claims, 2 Drawing Sheets

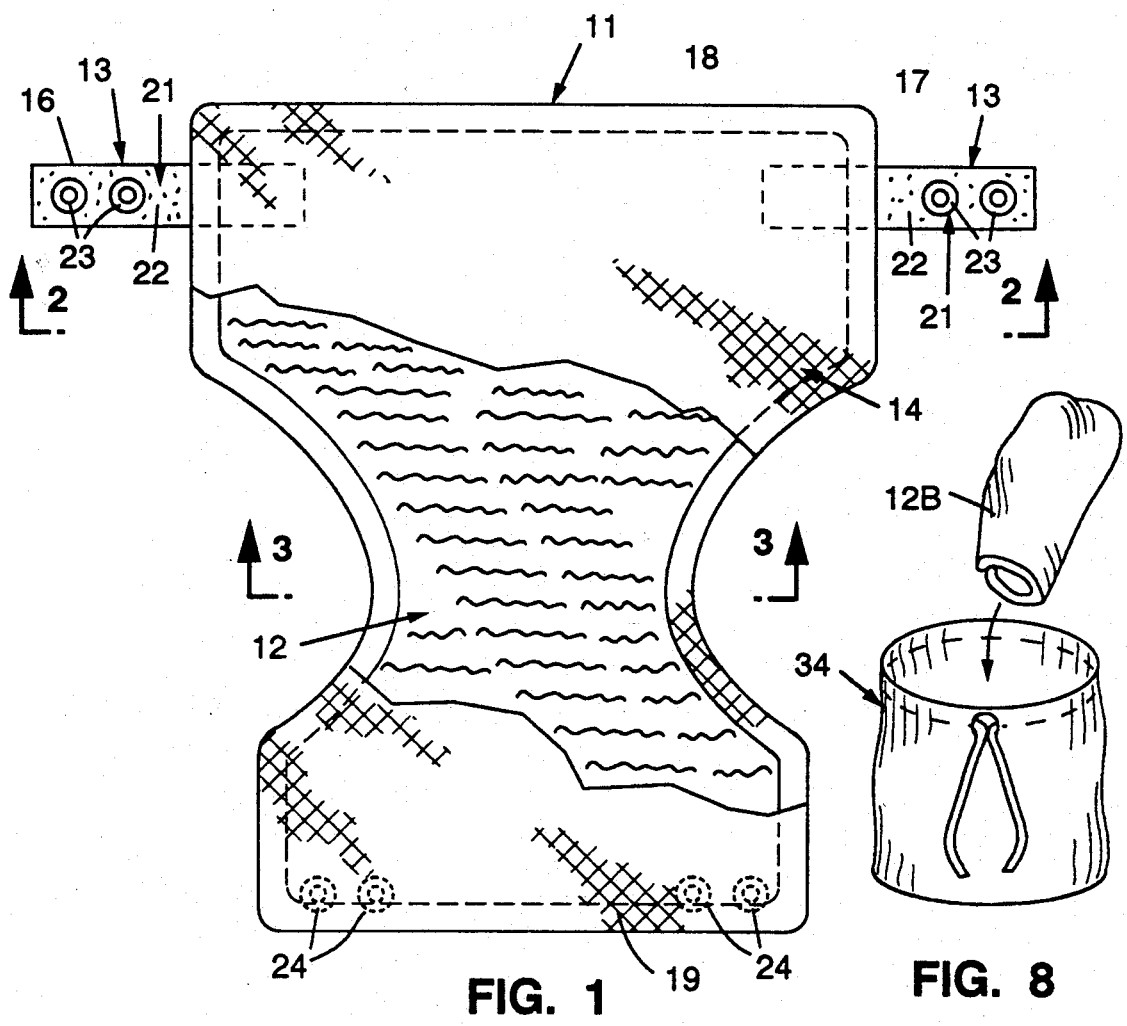
FIG. 1
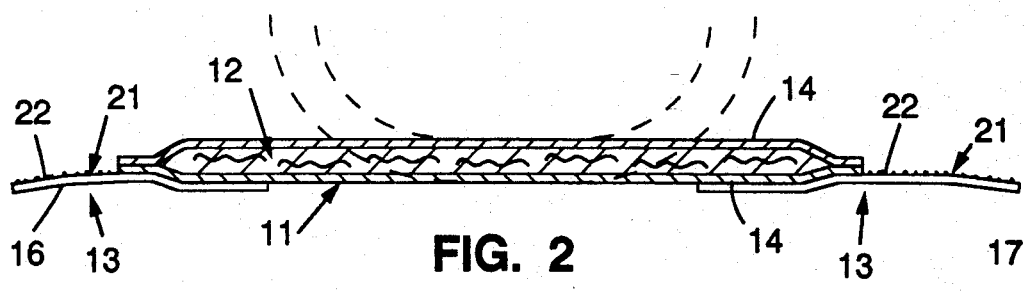
FIG. 8
FIG. 2
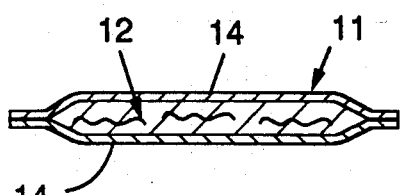
FIG. 3

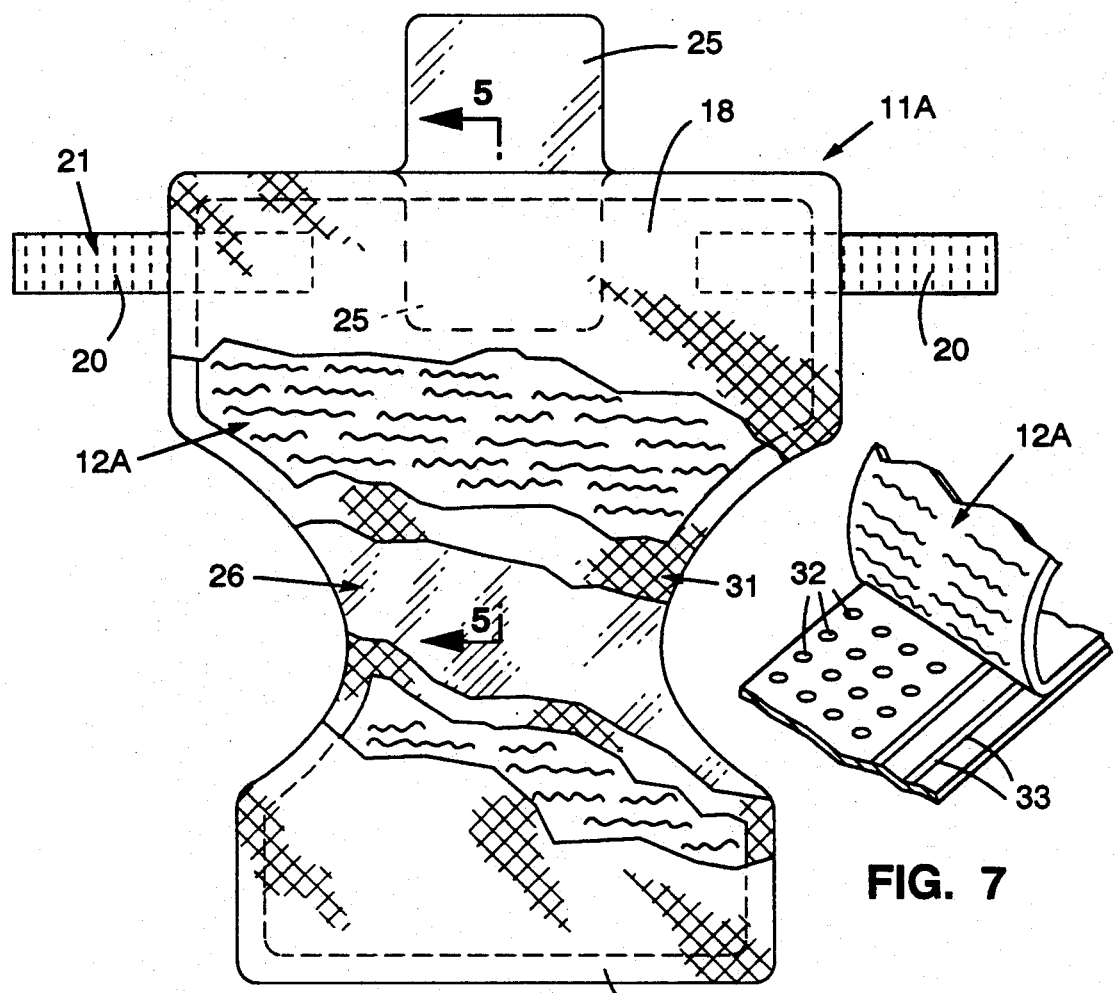
FIG. 4
FIG. 7
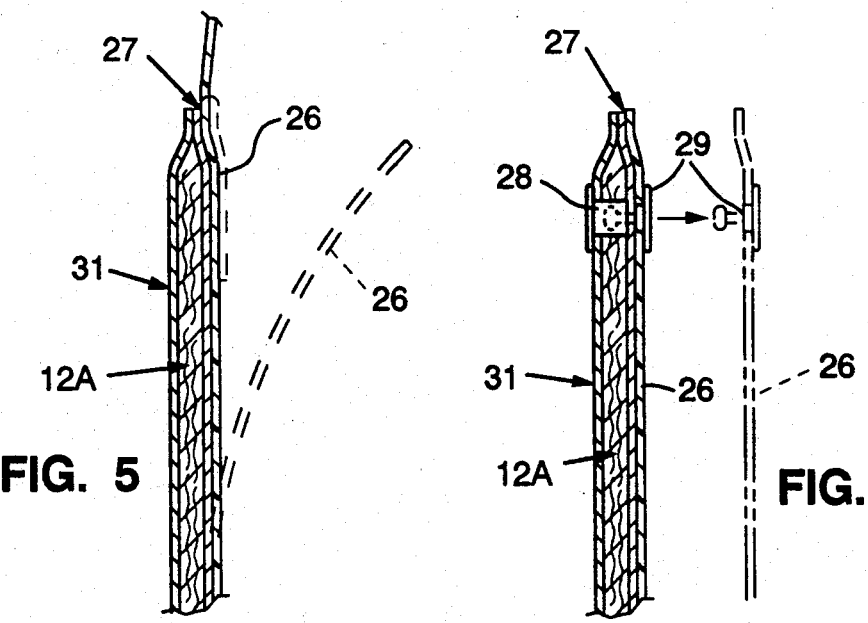
FIG. 5
FIG. 6

DISPOSABLE DIAPERS

BACKGROUND OF THE INVENTION

1. Field of the Invention

This invention relates to diapers and incontinence garments, and more particularly to such devices which are readily disposable.

2. Description of the Prior Art

Disposable diapers and incontinence garments, sometimes called adult diapers, have proven to be very convenient for the person taking care of the baby or incontinent person by eliminating any necessity for cleaning and washing the diapers in the manner hitherto necessary. As plastics and paper products have been improved in strength, absorbency and economy, more and more mothers and health care workers have begun to use composite diapers and incontinence garments made from layers of paperlike hydrophilic material bonded to a sheet plastic backing. In use, these diapers and undergarments are removed from the body of the wearer when they become wet or soiled and are forthwith consigned to the garbage can.

Unfortunately, disposal of such garbage, and other garbage containing plastics, has become an enormous problem. The plastic materials do not break down but remain in their original condition for many years, making it impossible for the garbage to be converted to usable soil by biological processes.

Attempts are being made to alleviate this problem by using plastics which are "biodegradable", that is, which can be broken down into their constituent elements by the action of microbes, sunlight and air. However, to date no truly biodegradable plastic material is known Even those plastics which are advertised as being biodegradable actually break down into a powder which itself is a growth impediment to biodegradability of the garbage.

Strong attempts are being made to overcome the problem of plastics in the garbage by requiring separation of all items made of plastic from the remainder of the garbage. This plastic is "recycled" by being reprocessed into a plastic material from which various items such as, for example, molded outdoor tables and chairs can be made.

Existing disposable diapers and incontinence garments or shields cannot be recycled successfully because of the large amounts of cellulose, plastic and other materials present therein.

Attempts have been made to mount a disposable moisture-absorbing insert pad in a shallow recess in a specially formed pants body made of plastic or rubber sheeting, for example see U.S. Pat. No. 3,081,772 issued Mar. 19, 1963 to H.C. Brooks et al. The disposable absorbent pad can easily be removed after use, but it is prone to shift around within the pants during use, and the structure required by the Brooks et al. patent is too expensive and bulky to be disposable.

Another attempt to provide a removable absorbent pad is found in U.S. Pat. No. 3,049,124 issued Aug. 14, 1962 to O. Thompson wherein the absorbent pad is secured by snap fasteners to a plastic outer pant which does not cover the entire hip area and which is secured in place on the wearer's body by four pairs of tie strings.

U.S. Pat. No. 4,576,601 issued Mar. 18, 1986 to Lucille M. Brain describes a complicated special diaper holder of vinyl material designed for holding cloth diapers. This patent states that a rectangular disposable pad with adhesive strips on the back could be substituted for the cloth diaper Other approaches to the problem of providing a disposable liner for diapers or incontinence garments are found in the following patents:

| Patent No. | Issue Date | Inventor |
|---|---|---|
| 3,050,063 | 08/21/62 | M. E. Margraf |
| 3,077,193 | 02/12/63 | B. J. Mann |
| 3,162,196 | 12/22/64 | G. Salk |
| 4,051,854 | 10/04/77 | G. L. Aaron |
| 4,244,368 | 01/13/81 | P. W. Caradonna |

The above-listed patents are believed to be relevant to the present invention because they were adduced by a prior art search made by an independent searcher, and a copy of each of the above-listed patents is supplied to the Patent and Trademark Office herewith.

SUMMARY OF THE INVENTION

The recyclable diaper or incontinence garment of the present invention in one of its forms includes a liquid impermeable layer of flexible material, a liquid absorbent layer of flexible material, and means for releasably connecting the liquid absorbent layer to the liquid impermeable layer in such manner that the liquid absorbent layer is easily separable from the liquid impermeable layer after use for separate recycling of the two layers. The liquid impermeable layer is formed of flexible sheet plastic, and the liquid absorbent layer is formed of flexible cellulose-based material After use and subsequent separation, the liquid impermeable layer is disposed of for recycling with other plastic materials, and the liquid absorbent layer is disposed of for recycling with cellulose-based material such as paper and the like.

The means for releasably connecting the liquid absorbent layer to the liquid impermeable layer may be of any suitable form capable of adhering the two layers together before and during use, and further capable of permitting easy separation of the two layers without adherence of plastic to cellulose material or cellulose material to plastic material A layer of pressure-sensitive adherent material on the plastic, liquid impermeable layer is preferred.

Other means for releasably connecting the liquid absorbent layer to the liquid impermeable layer may be provided, if desired, such as a plurality of fastening elements on the liquid absorbent layer releasably engageable with a plurality of fastening elements on the liquid impermeable layer. These fastening elements may be in the form of rows of snap fasteners, or strips of hook and eye material commonly known as VELCRO®. In either case, the fastening elements attached to the plastic layer and the fastening elements attached to the cellulosic layer must either be made of materials which are recyclable with the layer to which they are attached, or must be detachable from such layer. If VELCRO® is used, only strips of the fine multiple hooks need be used when the cellulose based absorbent layer is woven or felted loosely enough for the multiple hooks to releasably adhere thereto.

The plastic material of the liquid impermeable layer may be of any suitable kind which is thin enough, flexible enough, and non-toxic enough to perform its prescribed functions, and which is of a plastic material commonly recycled, for example, polyethylene.

The cellulose-based liquid absorbent layer may be of any suitable non-toxic and preferably non-allergenic material capable of absorbing and holding relatively large quantities of body waste liquids such as urine and watery feces. Suitable materials include paper fibers, cotton and rayon fibers, and other cellulosic materials, even including recycled paper and rags treated to eliminate undesirable contaminants.

The layer of liquid absorbent cellulose-based material may include paper-like materials having sufficient structural integrity to hold the shape of the absorbent layer and retain the liquid therein when the absorbent layer is stripped from the impermeable layer. A preferred form of liquid absorbent layer utilizes a liquid permeable flexible casing filled with fibrous cellulose material, the flexible casing being formed of a layer or layers of material having sufficient structural integrity to retain the fibrous cellulose material therein and to be releasably adhered to the impermeable layer so that, when the diaper or incontinence garment has been used and it is desired to separate the liquid absorbent layer from the liquid impermeable layer, the flexible casing is strong enough to be stripped away from the plastic impermeable layer while still retaining the saturated filler material in the casing.

In accordance with the invention, the liquid permeable casing is also formed of a cellulose-based material possessing sufficient strength, permeability, and structural integrity for the purposes described. For reasons of strength, it is preferred to use a felted or woven cloth formed from rayon fibers and woven or felted loosely enough to provide good liquid permeability therethrough.

In another form of the invention, the recyclable diaper or incontinence shield is made entirely of recyclable cellulose material and is worn inside conventional waterproof plastic or rubber pants. In this form of the invention, the liquid absorbent layer is formed substantially entirely of recyclable cellulose material and has a generally hour-glass shape adapted for mounting on the body of the user in covering relation to the area of the body between the waist and thighs, including the sides, genital, and anal areas. Fastening means is provided on the liquid absorbent layer, and this means also is formed of recyclable cellulose material and is further formed for releasably holding the liquid absorbent layer snugly about the user's body during use.

After use, the plastic or rubber pants are pulled down or removed, and the liquid absorbent layer is segregated with the paper garbage for recycling. The liquid absorbent layer is preferably formed of non-woven cellulose and is enclosed within liquid permeable flexible casing of cellulose based material adapted for recycling with the absorbent layer of non-woven cellulose. The casing is made of rayon cloth which is loosely felted or woven for making the rayon cloth more permeable to liquids emanating from the user.

The fastening means for releasably holding the liquid absorbent layer snugly about the user's body during use provides flexible tabs projecting laterally from each side of the liquid absorbent layer at one end thereof for engagement with the opposite end of the liquid absorbent layer when the diaper is mounted on the user, and releasable adherent means is provided on the flexible tabs to hold them in place until the absorbent layer is removed from the body of the user.

The adherent means preferably consists of a pressure-sensitive adhesive on the tabs, although the adherent means also may comprise a plurality of tiny hooks on the tabs releasably engageable with the rayon cloth of the casing. Alternatively, if desired, the fastening means may be in the form of a plurality of fastening elements, such as snap fasteners, attached to one end of the liquid absorbent layer and releasably engageable with a plurality of fastening elements attached to the other end of the liquid absorbent layer.

The preferred form of the recyclable diaper or incontinence shield of the present invention provides a liquid absorbent layer formed substantially entirely of recyclable cellulose material and having a generally hour-glass shape adapted for mounting on a human body in substantially covering relation to the body area between its waist and thighs, including the genital and anal areas, a liquid impermeable layer having a generally hour-glass shape of slightly larger dimensions that the liquid absorbent layer to provide a peripheral overlap when the liquid absorbent layer is mounted thereon, and means for releasably connecting the liquid absorbent layer to the liquid impermeable layer in such manner that the absorbent layer is easily separable from the impermeable layer for separate recycling after use.

It is therefore a principal object of the present invention to provide a disposable and recyclable diaper or incontinence shield construction having a liquid absorbent layer for receiving bodily liquids and wastes which is readily strippable from a liquid impermeable layer which protects the clothing and surroundings of the user until the diaper or shield is removed.

Another object of the present invention is to provide a recyclable diaper or incontinence shield of the character described in which all parts of the liquid absorbent layer are compatable with cellulose recycling processes.

A further object of the present invention is to provide a recyclable diaper or incontinence shield having a filler of cellulose fibers contained within a flexible casing which provides strength and stability and which is recyclable with the cellulose filler material.

A still further object of the present invention is to provide a recyclable diaper or incontinence shield construction of the character described in which the plastic and cellulose layers separate easily and cleanly for further separate recycling processing.

Another object of the present invention is to provide a recyclable diaper or incontinence shield of the character described in which an odor tight enclosure is provided for containing the used liquid absorbent layer against contaminating its surroundings, the enclosure being adapted for recycling along with the liquid absorbent layer.

Other objects and features of advantage will become apparent as the specification progresses, and from the claims.

BRIEF DESCRIPTION OF THE DRAWINGS

FIG. 1 is a plan view of a recyclable diaper or incontinence shield constructed in accordance with the present invention.

FIG. 2 is a cross-sectional view taken substantially on the plane of Line 2—2 of FIG. 1.

FIG. 3 is a cross-sectional view taken substantially on the plane of Line 3—3 of FIG. 1.

FIG. 4 is a plan view of a modified recyclable diaper or incontinence shield constructed in accordance with the present invention.

FIG. 5 is a cross-sectional view taken substantially on the plane of Line 5—5 of FIG. 4.

FIG. 6 is a view taken similarly to that of FIG. 5, but illustrating a different form of fastening means.

FIG. 7 is an enlarged fragmentary view of fastening elements utilized in a modified form of the invention.

FIG. 8 is a perspective view on a reduced scale of a container for enclosing used absorbent layers.

While only the preferred forms of the invention are illustrated in the drawings, it will be apparent that various modifications could be made without departing from the ambit of the claims.

DESCRIPTION OF THE PREFERRED EMBODIMENTS

As may be seen in the drawings, the recyclable diaper 11 of the present invention provides a liquid absorbent layer 12 formed substantially entirely of recyclable cellulose material and adapted for mounting on the body of a baby or incontinent person in covering relation to the area of the body between the waist and thighs, including the genital area, together with fastening means 13 on the liquid absorbent layer 12 also formed substantially entirely of recyclable cellulose material and adapted for releasably holding the liquid absorbent layer 12 snugly about the baby's body during use, the liquid absorbent layer 12 being adapted for wearing by the baby under separate pants (not shown) of liquid impervious sheet rubber or plastic material.

As here shown, the liquid absorbent layer 12 is formed of non-woven cellulose, preferably of hourglass shape and having maximum absorbency. If desired, certain conventional hydrophilic agents may be incorporated with the cellulose material, provided however that these agents are either cellulose based and recyclable with the cellulose absorbent material, or are capable of being washed away from the cellulose material during the initial stages of recycling.

The liquid absorbent layer 12 should be dimensionally stable and stay in place during use. Woven or felted cellulose fibers normally possess sufficient dimensional stability to maintain their structural integrity during use and afterwards prior to recycling. Where the liquid absorbent layer 12 is formed of non-woven cellulose, the loose cellulose material can be packed into a liquid permeable flexible casing 14 of cellulose based material adapted for recycling with the non-woven cellulose. This casing provides structural strength and integrity to avoid escape of the contaminated absorbent cellulose material.

The flexible casing 14 is preferably formed of a rayon cloth which is loosely woven for making it more permeable to liquid emanating from the body.

The fastening means 13 shown in FIGS. 1 through 3 are in the form of flexible tabs 16 and 17 projecting laterally from each side of the liquid absorbent layer 12 at one end 18 for engagement with the opposite end 19 when the diaper 11 is mounted on the body. Releasable adherent means 21 is provided on the flexible tabs so that when the end 19 of the diaper is drawn upward against the belly, the tabs 16 and 17 can be releasably adhered to the end 19 to hold the diaper snugly in place.

The adherent means 21 is preferably in the form of a layer of pressure sensitive adhesive 22 on the tabs 16 and 17 which releasably secures these tabs to the end 18 and the end 19 of absorbent layer 12. If desired, the tabs 16 and 17 may be detached from the diaper 11 entirely when the diaper is removed after use. In such case, the tabs could be disposed of separately and would not necessarily have to be made of recyclable cellulose.

Where it is desired not to use pressure-sensitive adhesive, the adherent means 21 can be in the form of a plurality of tiny hooks 20 releasably engageable with the rayon cloth of the casing 14. These hooks are preferably of the type found in the multiple hooks and loops attachable material known as VELCRO ®. The loosely woven rayon cloth of the casing 14 can releasably be engaged directly by the tiny hooks, in which case it is not necessary to provide the usual corresponding strips of tiny loops.

If additional strength is desired, the adherent means 21 can be in the form of the plurality of fastening elements 23 attached to the tabs 16 and 17 and releasably engageable with a plurality of fastening elements 24 attached to the end 19 of the liquid absorbent layer 12. As shown in FIG. 1 of the drawings, the fastening elements 23 and 24 constitute the male and female elements respectively of snap fasteners. It should be noted that in accordance with the invention these fastening elements 23 and 24 are also made of cellulose based recyclable material such as, for example, celluloid or cellophane. If non-cellulosic non-recyclable materials such as metals are used, the fastening elements 23 and 24 should be completely detachable from the diaper 11 for separate disposal.

In the form of the invention illustrated in FIGS. 4 through 6 of the drawings, the liquid absorbent layer 12 is releasably connected to a liquid impermeable layer 26, which eliminates the necessity for wearing rubber or plastic pants over the diaper. In accordance with the invention, releasable means 27 is provided for temporarily connecting the liquid absorbent layer 12 to the liquid impermeable layer 26 in such manner that the liquid absorbent layer 12 is easily separable from the liquid impermeable layer 26 after use for separate recycling. A tab 25 preferably extends from the layer 26 at end 18 for easy grasping by the person separating layers 26 and 12A. Tab 25 is folded back on itself at the rear until needed.

The liquid impermeable layer 26 may be of any suitable thin, flexible sheet material which is impervious to the passage of liquid therethrough. Preferably, the liquid impermeable layer 26 is formed of flexible sheet plastic which can be recycled with other plastic materials. Thin, sheet polyethylene is well adapted for use as the liquid impermeable layer 26.

The layer 12A shown in FIGS. 4 through 6 of the drawings is preferably similar to the liquid absorbent layer 12 shown in FIGS. 1 through 3 of the drawings. The layer 12A is formed of flexible cellulose based material capable of being recycled after use.

The releasable means 27 for temporarily connecting the liquid absorbent layer to the liquid impermeable layer 26 is preferably in the form of a pressure sensitive adhesive material which is adhered to both the liquid absorbent layer 12A and to the liquid impermeable layer 26. In order to facilitate complete separation of the absorbent layer 12A from the impermeable layer 26 after use, the adhesive, which may be pressure sensitive or not, is preferably disposed in a series of spaced fine dots 32 or strips 33 so that little or no absorbent cellulose material will adhere to the plastic layer 26, see FIG. 7 of the drawings.

In situations where it is desired not to use pressure sensitive adhesive, the releasable means 27 for temporarily connecting the liquid absorbent layer 12A to the liquid impermeable layer 26 is in the form of a plurality of fastening elements 28 on the liquid absorbent layer 12A which are releasably engageable with a plurality of mating fastening elements 29 on the liquid impermeable layer 26, see FIG. 6. The fasteners 28 and 29 cooperate to provide a plurality of snap fasteners. Here, again, as described in connection with the fastening elements 23 and 24 in FIGS. 1 through 3 of the drawings, the fastening elements 28 on the liquid absorbent layer 12A should be made of cellulose based, recyclable material, and the fastening elements 29 on the plastic layer 26 should be made of a plastic capable of being recycled with the material of the plastic layer 26. If snap fasteners made of other materials not compatible for recycling are used, they should be completely detachable from the liquid absorbent layer 12A and the liquid impermeable layer 26.

For increased strength and structural integrity, as discussed above in connection with the casing 14 of FIGS. 1 through 3, the absorbent cellulose material is preferably enclosed in a liquid permeable flexible casing 31, and the releasable means 27 is formed for releasably securing the casing 31 to the liquid impermeable layer 26. The casing 31 is formed of a cellulose based material preferably felted or woven rayon cloth.

In accordance with the invention, an odor tight and liquid proof container 34 is provided for receiving and enclosing the liquid absorbent layer 12 12A after use. Container 34 is made of liquid impervious cellulose based material which is recyclable with the used liquid absorbent layer 12B it contains. As shown in FIG. 8 of the drawings, container 34 is in the form of a bag or pouch having a closure draw-string, although it should be appreciated that other forms of liquid and odor proof containers recyclable with the contained used liquid absorbent layer can be used.

From the foregoing, it will be seen that the recyclable diaper construction of the present invention is well suited to perform its purpose of receiving and containing body waste from infants and from incontenent adults, and at the same time is well adapted for separating plastic and cellulose based materials so they can be segregated from the rest of the garbage for separate recycling both to conserve material and to eliminate large masses of non-biodegradable landfill.

What is claimed is:

1. A recyclable diaper, comprising:
a liquid impermeable, flexible layer of recyclable plastic material;
a liquid absorbent, flexible layer of recyclable cellulosic material; and
means for releasably connecting said liquid absorbent layer to said liquid impermeable layer while said diaper is being worn by a wearer yet allowing non-destruction separation of said layers immediately after said diaper is removed from the wearer by the person removing the diaper for subsequent separate cellulose and plastic disposal and recycling, respectively;
said means for releasably connecting said liquid absorbent layer to said liquid impermeable layer comprising a plurality of fastening means made of recyclable cellulosic material on said liquid absorbent layer and a plurality of cooperating fastening means made of recyclable plastic material on said liquid impermeable layer;
said fastening means and said cooperating fastening means being constructed and arranged for releasable engagement with each other while the diaper is being worn and non-destruction disengagement from each other immediately subsequent to the removal of the diaper from the wearer for disposal and recycling along with their respective layers.

2. A recyclable diaper as claimed in claim 1 wherein said means for releasably connecting said liquid absorbent layer to said liquid impermeable layer comprises a plurality of snap fasteners.

3. A recyclable diaper as claimed in claim 1 wherein a separate container of recyclable liquid impervious, cellulosic material is provided and proportioned for receiving and enclosing said liquid absorbent cellulosic layer after use so as to confine body wastes and their odors, said container being formed of cellulosic material recyclable with said absorbent layer.

4. A recyclable diaper as claimed in claim 1 further including fastening means for releasably holding said diaper about the body of the wearer during use comprising a plurality of recyclable cellulosic fastening elements attached to an end of said liquid absorbent layer and releasably engagable with a plurality of recyclable cellulosic fastening elements attached to another end of said liquid absorbent layer.

5. A recyclable diaper as claimed in claim 4 wherein said fastening means comprises a plurality of snap fasteners of recyclable cellulosic material.

* * * * *